(12) United States Patent
Hayashi et al.

(10) Patent No.: US 8,433,102 B2
(45) Date of Patent: Apr. 30, 2013

(54) SURFACE ROUGHNESS INSPECTION SYSTEM

(75) Inventors: Yoshinori Hayashi, Yokohama (JP); Hideki Mori, Yokohama (JP)

(73) Assignee: Shibaura Mechatronics Corporation, Yokohama-shi (JP)

( * ) Notice: Subject to any disclaimer, the term of this patent is extended or adjusted under 35 U.S.C. 154(b) by 808 days.

(21) Appl. No.: 12/086,081

(22) PCT Filed: Dec. 5, 2006

(86) PCT No.: PCT/JP2006/324264
§ 371 (c)(1),
(2), (4) Date: Feb. 27, 2009

(87) PCT Pub. No.: WO2007/066659
PCT Pub. Date: Jun. 14, 2007

(65) Prior Publication Data
US 2009/0177415 A1    Jul. 9, 2009

(30) Foreign Application Priority Data
Dec. 6, 2005    (JP) .................... 2005-352767

(51) Int. Cl.
*G06K 9/00*    (2006.01)

(52) U.S. Cl.
USPC ...................................................... 382/108

(58) Field of Classification Search .......... 382/100–108, 382/141–152; 348/86–90, 125–130; 700/95–212; 29/833–840; 438/16–20; 702/34–40
See application file for complete search history.

(56) References Cited

U.S. PATENT DOCUMENTS

| | | | | |
|---|---|---|---|---|
| 5,078,954 A | * | 1/1992 | Smith et al. | 376/245 |
| 5,835,220 A | * | 11/1998 | Kazama et al. | 356/369 |
| 6,782,140 B1 | * | 8/2004 | Kaneko | 382/282 |
| 2004/0196453 A1 | * | 10/2004 | Some | 356/237.1 |
| 2005/0036671 A1 | * | 2/2005 | Watkins et al. | 382/145 |

FOREIGN PATENT DOCUMENTS

| | | |
|---|---|---|
| JP | 11-281337 | 10/1999 |
| JP | 2003-243465 | 8/2003 |

OTHER PUBLICATIONS

Notification of Reasons for Refusal received in counterpart application No. 2007-549135 from the Japanese Patent Office dated Jan. 25, 2012 with English translation (6 pages).

* cited by examiner

*Primary Examiner* — Atiba O Fitzpatrick
(74) *Attorney, Agent, or Firm* — Kratz, Quintos & Hanson, LLP

(57) ABSTRACT

[Problem] To provide a surface roughness inspection system enabling suitable inspection even when the surface of the object being inspected is curved.
[Means for Solution] A system having an imaging unit 20 having a line sensor 22 and scanning the surface of an object being inspected 101 in a direction perpendicular to the direction of extension of the line sensor 22 and outputting a density signal for each pixel from the line sensor 22 and a processing unit 50 processing the density signal from the line sensor 22 of the imaging unit 20, the processing unit 50 having a means for acquiring a pixel density value based on a density signal from the line sensor 22 (S2) and a density state generating means for generating a density state information Pf showing the density state in the scan direction of the object surface based on all of the pixel density values acquired for the object surface 101 being inspected (S7).

6 Claims, 12 Drawing Sheets

(a)

(b)

(a)

(b)

(c)

(a)

(b)

SURFACE ROUGHNESS INSPECTION SYSTEM

TECHNICAL FIELD

The present invention relates to a surface roughness inspection system detecting the roughness of a surface of an object being inspected such as a peripheral end face of a semiconductor wafer.

BACKGROUND ART

In the past, an inspection system for detecting the roughness of the surface of an object being inspected has been proposed (for example, see Patent Document 1). In this type of inspection system, a laser beam is fired at the surface of an object being inspected and the amount of laser beam scattered and reflected at that object surface is measured. Furthermore, information showing the surface roughness of the object surface is generated based on the measured amount. According to this inspection system, it becomes possible to objectively inspect the surface roughness of a semiconductor wafer etc.
Patent Document 1: Japanese Patent Publication (A) No. 6-244261

DISCLOSURE OF THE INVENTION

Problems to be Solved by the Invention

However, the conventional inspection system inspects a flat surface such as the surface of a semiconductor wafer. When inspecting a curved surface such as a peripheral end face of a semiconductor wafer, suitable inspection is difficult. For example, when inspecting the peripheral end face of a semiconductor wafer, it is necessary to set the size of the laser spot to at least the thickness of the semiconductor wafer (about 700 μm to 2 mm), but if setting the size of the laser spot in that way, due to the effect of the degree of curvature of the peripheral end face, it is not possible to suitably receive the laser beam scattered at that peripheral end face. Therefore, unless adjusting the sensitivity of the light receiving element or otherwise suitably changing the measurement conditions, suitable data cannot be acquired.

The present invention was made so as to solve this problem in the prior art and provides a surface roughness inspection system able suitably inspect even a curved surface of an object being inspected.

Means for Solving the Problems

The surface roughness inspection system according to the present invention has an imaging unit having a line sensor, scanning a surface of an object being inspected in a direction perpendicular to a direction of extension of the line sensor, and outputting a density signal for each pixel from the line sensor and a processing unit processing a density signal from the line sensor of the imaging unit, the processing unit having a means for acquiring a pixel density value based on the density signal from the line sensor and a density state generating means for generating density state information showing the state of density at a scan direction of the object surface based on all of the pixel density values acquired for the surface of the object being inspected.

Due to this configuration, since the width of a line sensor is extremely small, even if the surface of the object being inspected is curved, by suitably setting the direction of curvature of the object surface and the orientation of the line sensor, it is possible to scan the object surface in the direction perpendicular to the direction in which the line sensor extends in the state greatly eliminating the effect of the degree of curvature of the object surface. Furthermore, when that line sensor (imaging unit) scans the object surface, the pixel density value is acquired for each pixel based on the density signal output from the line sensor, and density state information expressing the state of density in the scan direction of the object surface is generated based on all of the pixel density values acquired for the object surface. The level of the density signal output from the line sensor changes due to the direction of the local surface of the object surface or relief shapes etc., so the density state information obtained based on the density signal from such a line sensor can express the state of roughness of the surface of an object being inspected in the scan direction.

Further, the surface roughness inspection system according to the present invention can be configured so that the processing unit has a display control means for making a display unit display a profile of density in a scan direction of the object surface based on the density state information.

Due to this configuration, the display unit displays a profile of the density in the scan direction of the object surface, so the operator can view that profile and judge the roughness in the scan direction of the object surface.

Further, the surface roughness inspection system according to the present invention can be configured so that the processing unit has a judging means for judging the roughness of the object surface based on the density state information.

Due to this configuration, the roughness of the object surface is judged based on the density state information able to show the state of roughness of the surface of the object being inspected in the scan direction of the line sensor, so it becomes possible to judge the roughness of the object surface based on the judgment results.

Furthermore, the surface roughness inspection system according to the present invention can be configured so that the density state generating means has a processing means shifting a one or more scan line window set with respect to image information expressed by all of the pixel density values acquired for the surface of an object being inspected in the scan direction of the object surface and calculating an area density value representing that window based on all of the pixel density values in the window at each scan position and generates the density state information based on the area density value at each scan position.

Due to this configuration, density state information is obtained based on the area density value calculated based on all of the pixel density values in the window, so by suitably setting the width of the window (number of lines), it is possible to judge the roughness of the object surface based on the density state information from a greater perspective.

Further, the surface roughness inspection system according to the present invention can be configured so that the processing means computes the sum of all of the pixel density values in the window as an area density value.

Due to this configuration, since the area density value representing the window is obtained by adding up all of the pixel density values in the window, it is possible to easily obtain that area density value.

Further, the surface roughness inspection system according to the present invention can be configured by having a window setting means setting a width of the window in the scan direction.

Due to this configuration, it is possible to set various widths of the window, so it is possible to judge the roughness of an object surface under various conditions.

Further, the surface roughness inspection system according to the present invention can be configured by having the object being inspected be a semiconductor wafer, having the line sensor arranged to extend in a direction substantially vertical to the surface of the semiconductor wafer, and making the semiconductor wafer turn about an axis vertical to the surface so as to scan that peripheral end face of the semiconductor wafer.

Due to this configuration, when the line sensor is scanning the peripheral end face of the semiconductor wafer in the peripheral direction, the pixel density value is acquired for each pixel based on the density signal output from the line sensor, and density state information showing the state of the density in the scan direction of that peripheral end face is generated based on all of the pixel density values acquired for the peripheral end face of the semiconductor wafer. Furthermore, that density state information can express the state of roughness of the peripheral end face of the semiconductor wafer in the scan direction (peripheral direction).

Effects of the Invention

According to the surface roughness inspection system according to the present invention, it becomes possible to scan the object surface in a direction perpendicular to the direction in which the line sensor extends in the state greatly eliminating the effect of the degree of curvature of the object surface. Density state information able to express the state of roughness in the scan direction of the object surface is generated based on the density signal output from that line sensor, so it becomes possible to suitably inspect the surface roughness even if the surface of the object being inspected is a curved surface.

Figure 1:
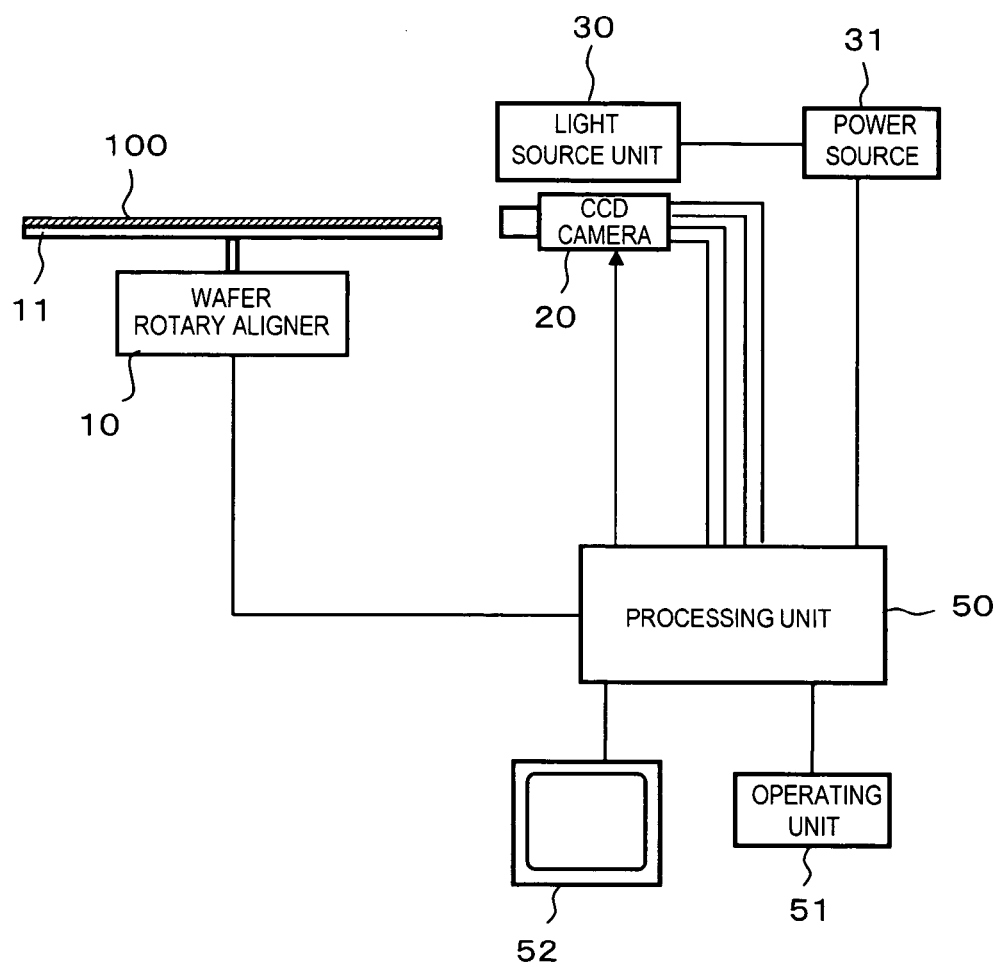
FIG. 1 is a view showing the configuration of a surface roughness inspection system according to an embodiment of the present invention.

DESCRIPTION OF NOTATIONS 10 wafer rotary aligner
11 turntable
20 CCD camera
21 lens system
22 line sensor
30 light source unit
31 power source
50 processing unit
51 operation unit
52 monitor unit
100 semiconductor wafer
101 peripheral end face

BEST MODE FOR CARRYING OUT THE INVENTION

Below, embodiments of the present invention will be explained based on the drawings.

The embodiments of the surface roughness inspection system according to the present invention are configured as shown in FIG. 1. This surface roughness inspection system inspects the surface roughness of the peripheral end face of a semiconductor wafer.

In FIG. 1, this surface roughness inspection system has a wafer rotary aligner 10. This wafer rotary aligner 10 turns a turntable 11 on which a semiconductor wafer 100 being inspected is set. Further, a CCD camera 20 (imaging unit) is set so as to become a predetermined positional relationship with respect to the peripheral end face of the semiconductor wafer 100 set on the turntable 11, and a light source unit 30 emitting diffused light by the supply of power from a power source 31 is set so as to irradiate the peripheral end face of the semiconductor wafer 100 falling in the range of capture of the CCD camera 20 by the diffused light.

Further, this surface roughness inspection system has a processing unit 50, also referred to herein as a processor. The processing unit 50 controls the wafer rotary aligner 10 based on the operation of the operation unit 51 to make the turntable 11 turn by a predetermined speed and processes the density signal for each pixel output from the CCD camera 20. The processing unit 50 can make a monitor unit 52 (display unit) display an image of the peripheral end face of the semiconductor wafer 100 and various information based on the density signal of each pixel from the CCD camera 20.

Figure 2:
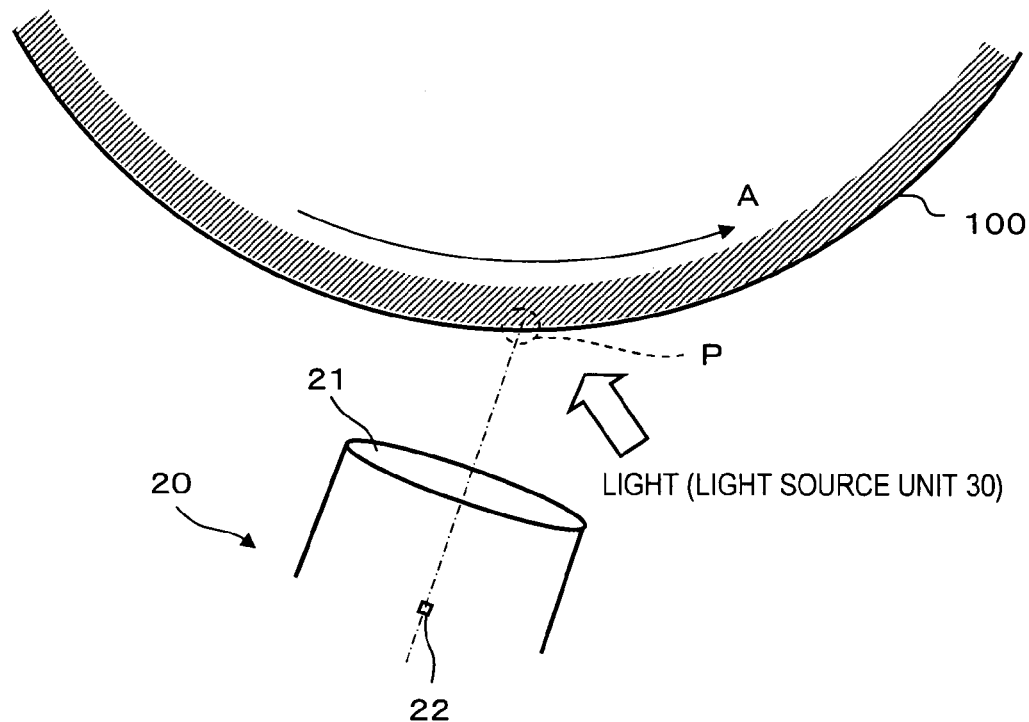
FIG. 2 gives a plan view (a) showing the positional relationship between a line sensor in a CCD camera in the surface roughness inspection system shown in FIG. 1 and a semiconductor wafer being inspected and a side view (b) showing the positional relationship between the line sensor and a peripheral end face of a semiconductor wafer.
Figure 2:
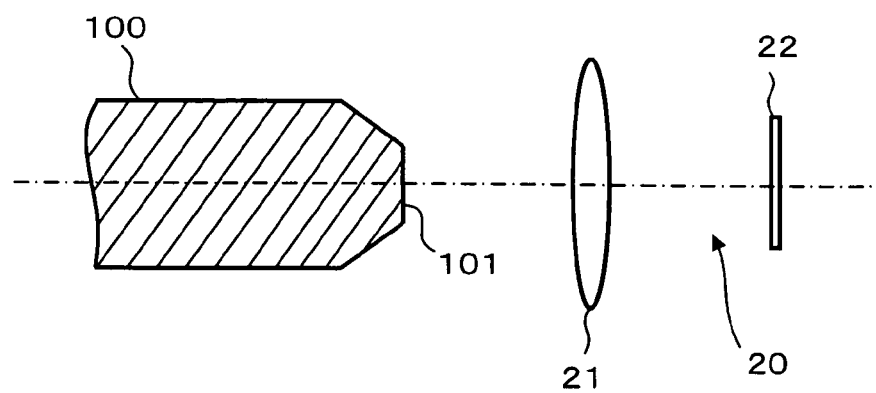

The CCD camera 20, as shown in FIGS. 2(a) and (b), is provided with a lens system 21 (object lens) and a line sensor 22 (single color CCD line sensor). The CCD camera 20, as shown in FIG. 2(b), is set so as to face the peripheral end face 101 of the semiconductor wafer 100 so that the line sensor 22 extends along the direction substantially vertical to the surface of the semiconductor wafer 100. Further, the CCD camera 20 is set in orientation, as shown in FIG. 2(a), so that the light reflected from the light irradiated portion P of the peripheral end face of the semiconductor wafer 100 irradiated by the light from the light source unit 30 can be effectively received by the line sensor 22.

Since the positional relationship between the line sensor 22 and the peripheral end face 101 of the semiconductor wafer 100 being inspected is set in the above way (see FIGS. 2(a), (b)), an extremely fine (for example, 3 μm) scan line of the line sensor 22 is set in a direction substantially vertical to the surface of the semiconductor wafer 100 (vertical surface), that is, perpendicular to the peripheral direction of the peripheral end face 101. Due to this, the line sensor 22 can scan the peripheral end face 101 in the peripheral direction in the state eliminating the effects of the degree of curvature of the peripheral end face 101 of the semiconductor wafer 100.

Figure 3:
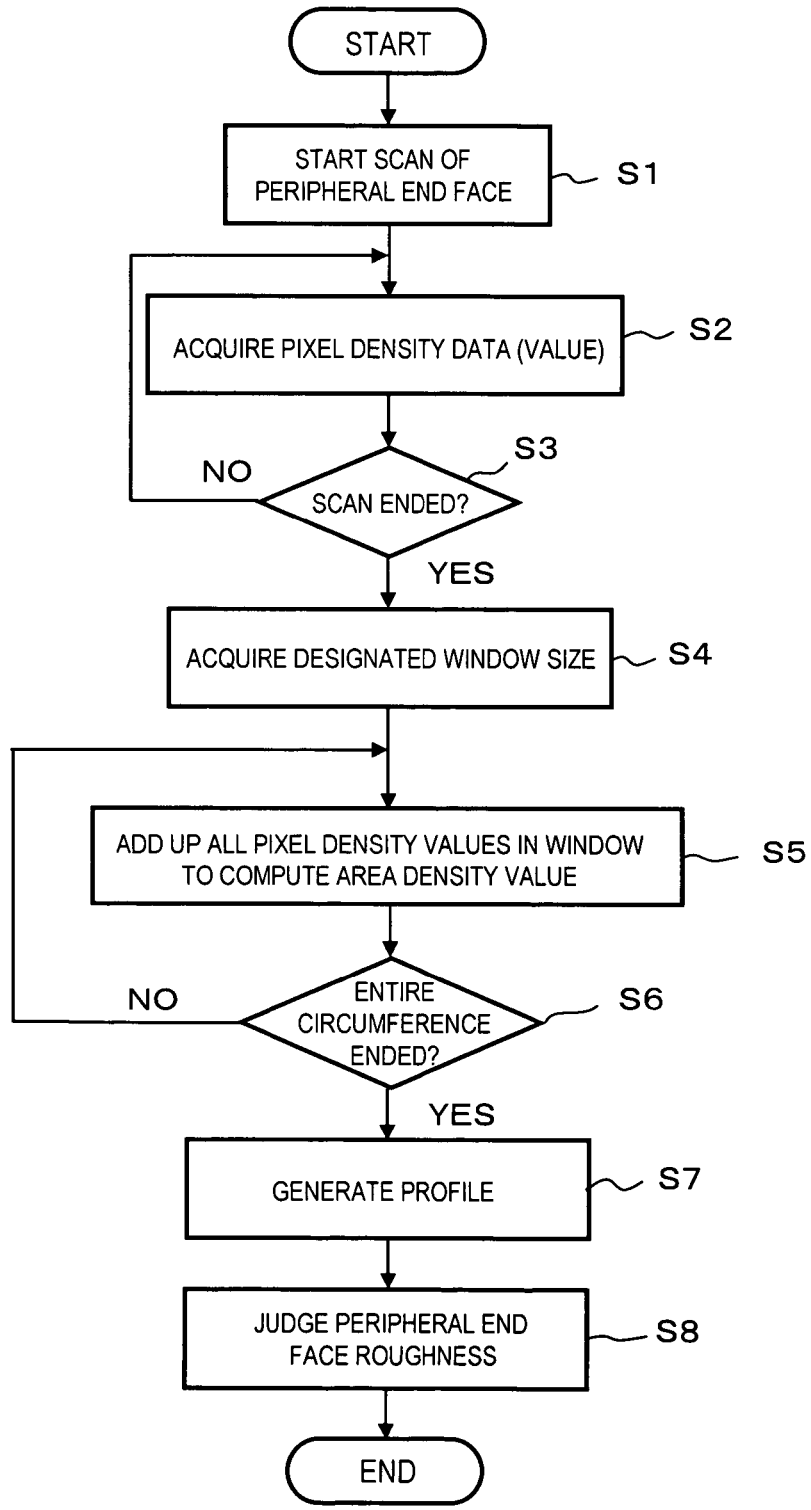
FIG. 3 is a flowchart showing a processing routine at a processing unit in the surface roughness inspection system shown in FIG. 1.

The processing unit 50 executes processing according to the routine shown in FIG. 3.

In FIG. 3, the processing unit 50 controls the wafer rotary aligner 10 and makes the turntable 11 turn when a predetermined start operation is performed by the operation unit 51. Along with turning of this turntable 11, the semiconductor wafer 100 turns at a predetermined speed and the scan of the peripheral end face 101 by the CCD camera 20 of the semiconductor wafer 100 is started (S1). In the process of scanning that peripheral end face 101, the processing unit 50 receives as input the density signal for each pixel successively output from the line sensor 22 of the CCD camera unit 20, converts that density signal into pixel density values, and stores the same in a predetermined memory (S2). Furthermore, the processing unit 50 judges if the semiconductor wafer 100 has made one turn and the scan for the entire circumference of the end face has ended (S3) and repeatedly executes the processing (S2).

Figure 4:
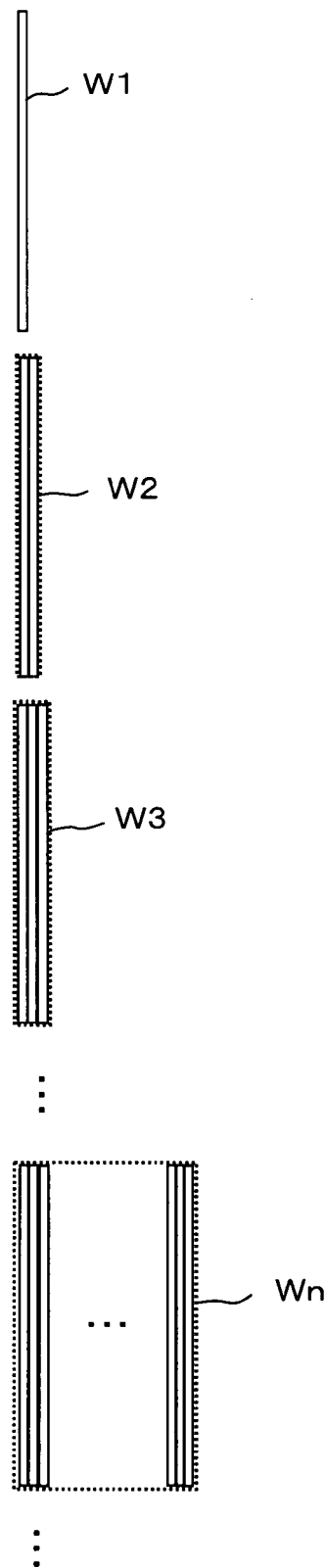
FIG. 4 is a view showing windows W1 to Wn differing in widths.

When the processing unit 50 judges that the scan of the entire circumference of the end face of the semiconductor wafer 100 has ended (YES at S3), it acquires the size of the window designated by the operation of the operation unit 51 (S4). As shown in FIG. 4, a one or more scan line window formed on the peripheral end face 101 of the semiconductor wafer 100 by the line sensor 22 can be set. That is, a one scan line window W1, two scan line window W2, three scan line window W3, . . . , n number scan line window Wn, etc. can be designated. Note that at the time when the scan of the entire circumference of the end face of the semiconductor wafer 100 has ended, all of the pixel density values obtained over the entire circumference of that end face are loaded in the memory as image information showing the total circumference (0° position to 360° position) of the peripheral end face of the semiconductor wafer 100.

Figure 5:
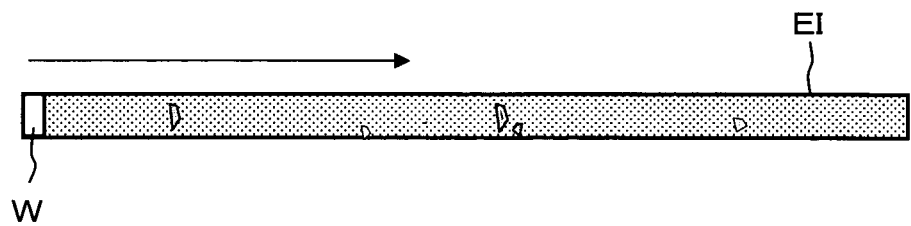
FIG. 5 is a view showing a window W set for image information EI.

The processing unit 50, as shown in FIG. 5, sets the designated size of the window W in order from the scan position (0°) for the image information ZEI composed of all of the pixel density values loaded in the memory, adds (cumulatively) all of the pixel density values included in that window W, and calculates that sum as the area density value representing that window W (S5). Furthermore, the processing unit 50 judges if the processing of the image information EI corresponding to the entire circumference of the end face has ended (S6) and repeatedly executes the processing (S5) while shifting the window W.

Figure 6:
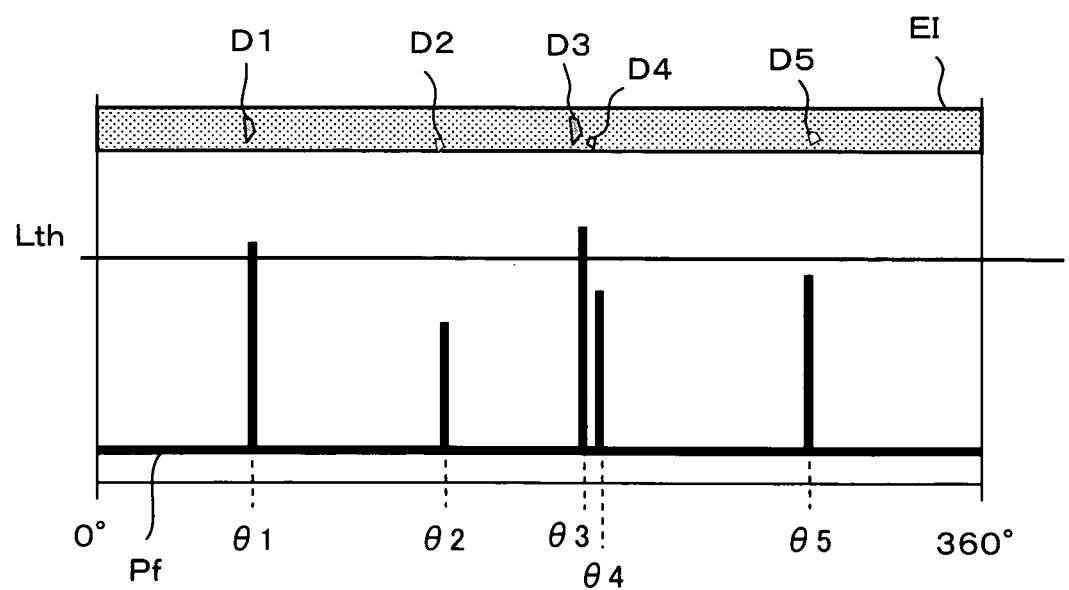
FIG. 6 is a graph showing profile information.

When the processing unit 50 judges that the processing of the image information EI corresponding to the entire circumference of the end face has ended (YES at S6), for example, it links the scan position (θ) and the area density value obtained for the window W set at each scan position and generates profile information regarding the density as the density state information showing the state of density in the scan direction of the peripheral end face 101 of the semiconductor wafer 100 being inspected. For example, as shown in FIG. 6, if the image information EI includes portions D1, D2, D3, D4, and D5 where the density levels greatly differ compared with the density level of the background, profile information Pf where the area density values at the scan positions θ1, θ2, θ3, θ4, θ5 corresponding to those portions stick out is obtained. The position resolution in this profile information is determined by the set width of the window W.

The processing unit 50, when generating profile information (density state information) regarding the density in the above way, uses that profile information to perform processing for judging the roughness of the peripheral end face 101 of the semiconductor wafer 100 being inspected (S8). The local surface slant, relief shapes, etc. of the peripheral end face 101 of the semiconductor wafer 100 causes changes in the level of the density signal output from the line sensor 22, so the profile information (density state information) obtained based on the density signal from the line sensor 22 shows the state of roughness of the peripheral end face 101 of the semiconductor wafer 100 in the scan direction.

Therefore, in the roughness judgment processing (S8), it is judged if the area density value at each scan position in the profile information exceeds a predetermined threshold value Lth. Furthermore, it is judged that the surface of the portion of the peripheral end face 101 corresponding to a scan position with an area density value exceeding that threshold value Lth is particularly rough and that, at that portion, there is a scratch or other defect. For example, from the profile information shown in FIG. 6, it is judged that the surfaces of the portions of the peripheral end face 101 corresponding to the scan positions θ1 and θ3 with area density values exceeding the threshold value Lth are particularly rough and that, at those portions, there are scratches or other defects.

Further, the processing unit 50, together with the roughness judgment processing (S8), can make the monitor unit 52 display the profile of the roughness based on the profile information (display control). In this case, for example, the profile Pf shown in FIG. 6 is displayed on the monitor unit 52, so the operator can judge the state of roughness of the peripheral end face 101 of the semiconductor wafer 100 being inspected based on the profile Pf displayed on the monitor unit 52.

Figure 7:
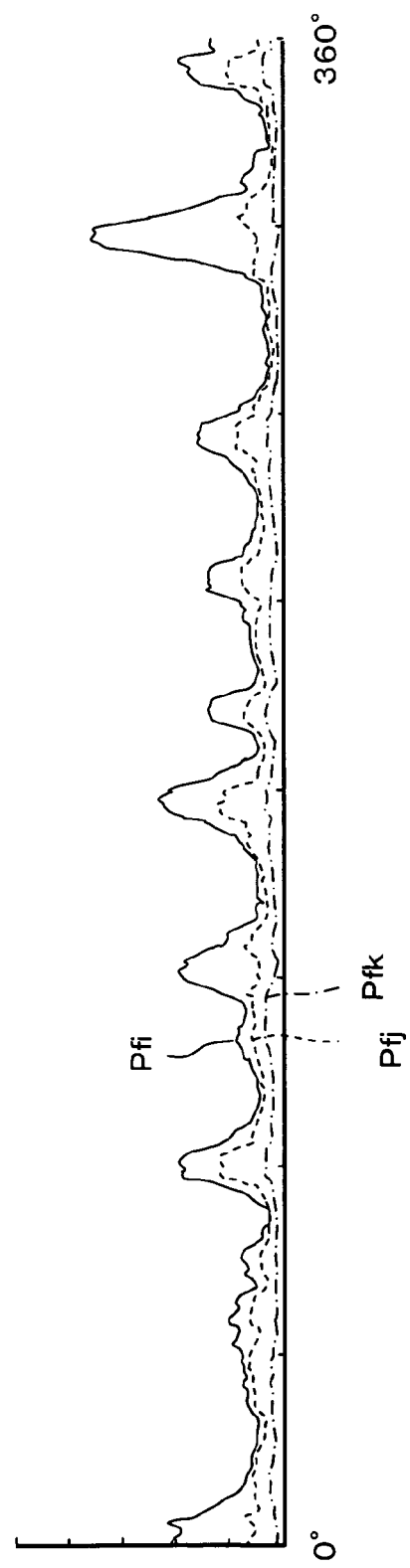
FIG. 7 is a view showing a plurality of profiles obtained by setting windows of different widths.

Further, the roughness judgment processing (S8) is not limited to the above-mentioned processing. For example, as shown in FIG. 7, by comparing the profile information Pfi, Pfj, and Pfk obtained for a plurality of windows Wi, Wj, and Wk of different widths, the peripheral end face 101 of the semiconductor wafer 100 can be judged for roughness. The profile information obtained for a wide width window can express the state of the relatively low frequency component of the image information EI. Further, the profile information obtained for a narrow width window can express the state of the relatively high frequency component of the image information EI. In this way, by comparing the states of the different frequency components of the image information EI, the peripheral end face 101 of the semiconductor wafer 100 can be judged for roughness. For example, when the plurality of profile information Pfi, Pfj, and Pfk corresponding to the different frequency components of the image information EI fluctuate in the same way, the peripheral end face 101 can judge that the surface is relatively stable. On the other hand, when the deviation in scan positions of the peak values at the plurality of profile information Pfi, Pfj, and Pfk corresponding to the different frequency components of the image information EI is large, it can be judged that the portions of the peripheral end face 101 corresponding to the vicinities of the scan positions are rough.

Furthermore, in the roughness judgment processing (S8), it is possible to calculate parameters corresponding to the parameters showing the roughness prescribed in the JIS from the obtained profile information as shown in FIGS. 8(a), (b), and (c) and judge the roughness of the peripheral end face 101 of the semiconductor wafer 100 by that parameter. Note that the profiles shown in FIGS. 8(a), (b), and (c) are for the peripheral end face 101 of the semiconductor wafer 100 of a diameter of about 30 cm. The total peripheral length L from the scan position (0°) to the scan position (360°) becomes about 1000 mm.

Figure 8:
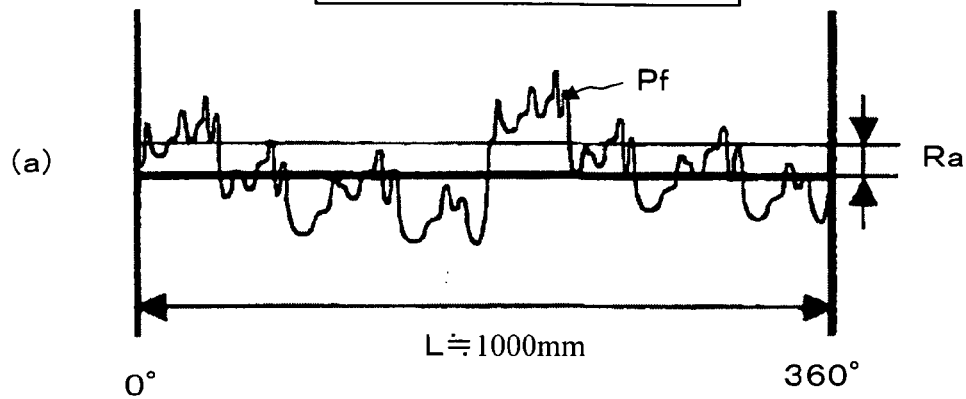
FIG. 8 is a view showing various parameters showing the roughness prescribed in JIS.
Figure 8:
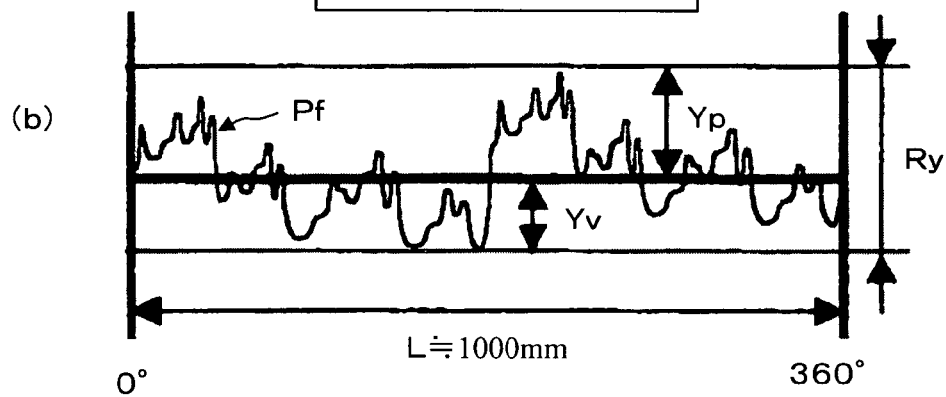
Figure 8:
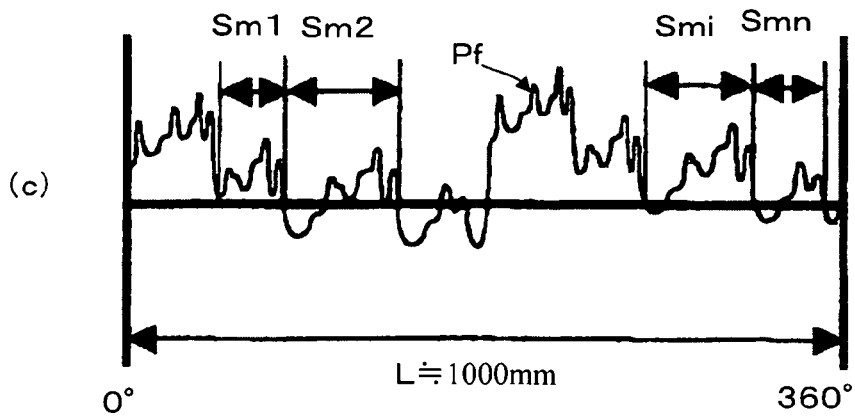

In the example shown in FIG. 8(*a*), it is possible to calculate the parameter corresponding to the arithmetic average roughness Ra prescribed in JIS B0601-1994 in accordance with equation (1). In the example shown in FIG. 8(*b*), it is possible to calculate the parameter corresponding to the maximum height Ry prescribed in JIS B0601-1994 in accordance with equation (2). Further, in the example shown in FIG. 8(*c*), it is possible to calculate the parameter corresponding to the mean span Sm of the relief shapes prescribed in JIS B0601-1994 in accordance with equation (3).

According to the above-mentioned surface roughness inspection system, it becomes possible to scan the peripheral end face 101 in a direction perpendicular to the direction along which the line sensor 22 extends in a state eliminating the effect of the degree of curvature of the peripheral end face 101 of the semiconductor wafer 100 being inspected, and Profile information able to show the state of roughness in the scan direction (peripheral direction) of the peripheral end face 101 (see FIG. 6 to FIG. 8) is generated based on the density signal output from that line sensor 22, so that it becomes possible to suitably inspect the surface roughness even if the peripheral end face 101 of the semiconductor wafer 100 is curved.

In the above-mentioned example, profile information was generated using the area density value of each window, but the invention is not limited to this. For example, it is also possible to generate profile information based on the moving average of the area density value for a plurality of windows (for example, the value obtained by averaging the area density values while shifting a window one pixel worth at a time).

The above-mentioned roughness judgment processing (S8 in FIG. 3) will be explained in further detail. Further, the result in this judgment processing can be utilized for confirming the endpoint of the process for mirror polishing the wafer end face (endpoint of polishing).

Figure 9:
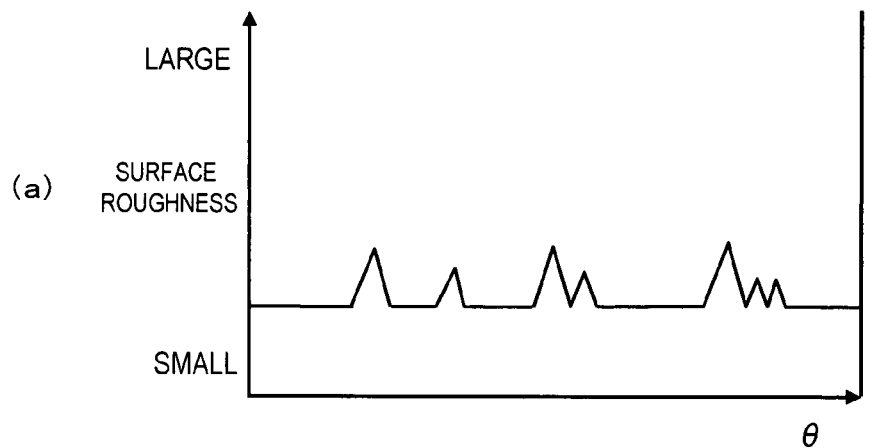
FIG. 9 is a view explaining a technique for judging the surface roughness for a bare wafer.
Figure 9:
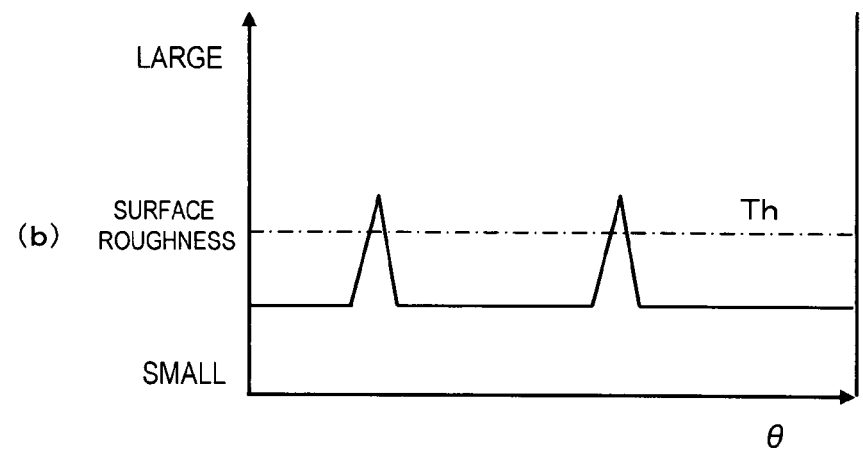
Figure 9:
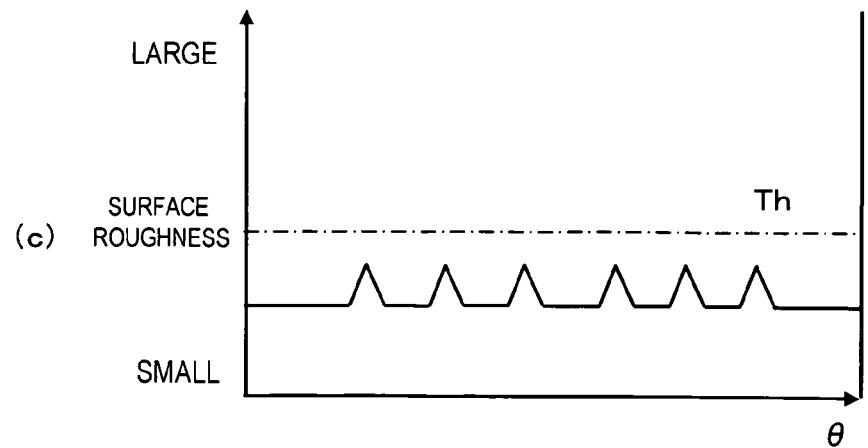

When the semiconductor wafer 100 being inspected is a bare wafer, there is a large amount of light reflected at the surface and the density level becomes low. Therefore, in this case, for example, as shown in FIG. 9(*a*), profile information showing the area density value corresponding to each scan position (θ) prepared by a predetermined window width W becomes a relatively low density level of the background. In roughness judgment processing predicated on profile information of a relatively low density level of the background, a relatively low level judgment line Th (threshold value) is set.

Due to this, for example, as shown in FIG. 9(*b*), from profile information partially including the density level exceeding the judgment line Th, it is possible to judge objects where the surface roughness is not uniform and the state of polishing is not that good. Further, from profile information that parts where the density level exceeding the judgment line Th are uniformly present across the entire scan position (0 degree to 360 degrees), the extent of polishing is still not sufficient, but it is possible to judge that the roughness of the surface is uniform. Furthermore, as shown in FIG. 9(*c*), from profile information with no locations where the density level exceeds the judgment line Th, it is possible to judge that the surface roughness is uniform and the endpoint of the polishing has been reached.

Next, when the semiconductor wafer 100 being inspected is, for example, a product wafer on which a film is formed, the light reflected at the surface is affected by the film and the density level becomes higher than the case of a bare wafer.

Figure 10:
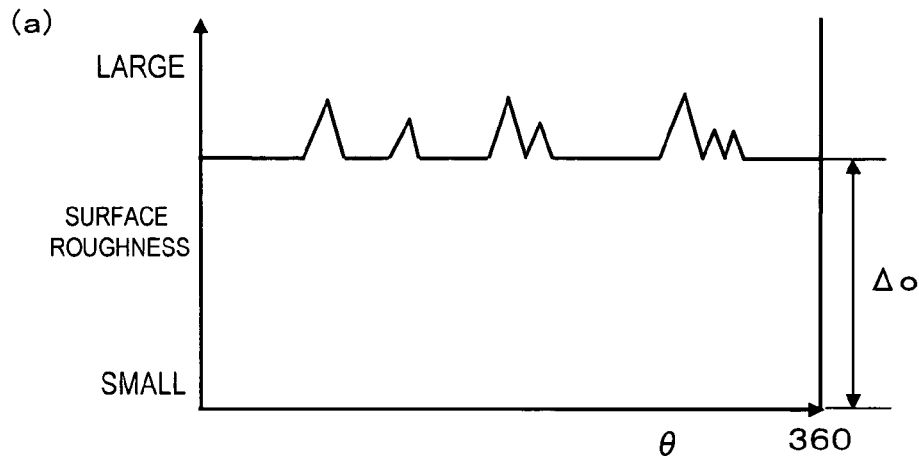
FIG. 10 is a view explaining a technique for judging the surface roughness for a product wafer on which a film is formed.
Figure 10:
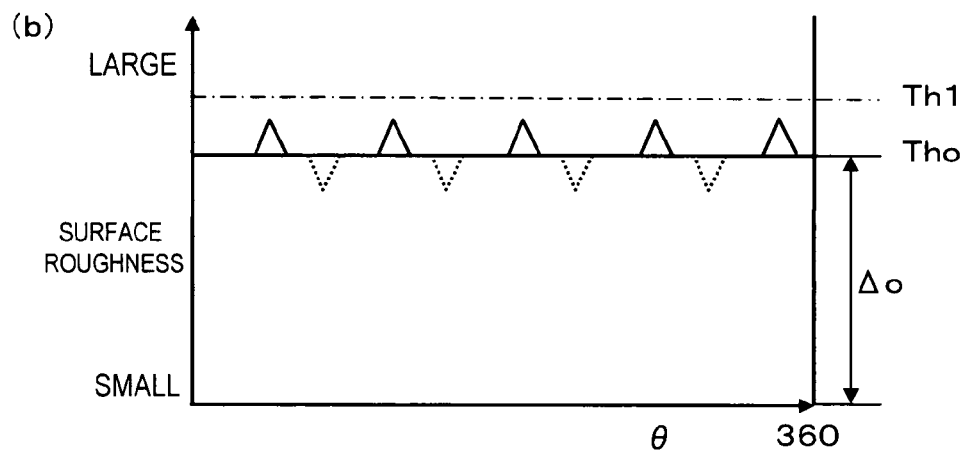
Figure 10:
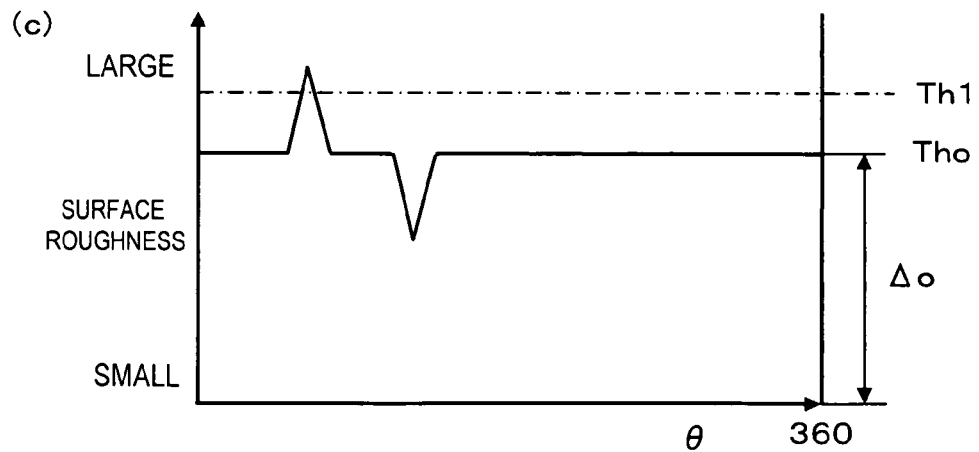

Therefore, in this case, for example, as shown in FIG. 10(*a*), the profile information becomes a high density level overall. For this reason, in the above-mentioned way, it is not possible to use the judgment line Th used for processing for inspection of a bare wafer as is for the case of inspection of a product wafer.

The difference between the profile information for a bare wafer (see FIG. 9(*a*)) and the profile information for a product wafer formed with a film (see FIG. 10(*a*)) is due to the offset value Δo based on the difference of the density level of the background. Therefore, by finding this amount of offset Δo, it is possible to judge the surface roughness of a product wafer by the same judgment reference (judgment line Th) as the surface roughness of a bare wafer.

The density level of the background can be viewed as being substantially constant over the entire scan position (θ). Therefore, the profile informations obtained by changing the window width W in various ways have frequency characteristics in accordance with the window width W, but the part corresponding to the density level of the background becomes substantially the same density level no matter what the frequency characteristic of the profile information. From this, for example, it is possible to generate a plurality of profile information for a semiconductor wafer 100 and set the lowest density level among the density levels becoming substantially the same in the different profile information as the offset value Δo.

For example, it is possible to use the thus determined offset value Δo and the judgment level Th used in the case of a bare wafer to determine a new judgment value Th1 in accordance with $$Th1 = Th + \Delta o \tag{1}$$

In this case, for example, as shown in FIG. 10(*b*), even if the overall density level is high, it is possible to judge that the surface roughness is uniform and that the endpoint of polishing has been reached from profile information with no locations of a density level over a judgment line Th1 (other than broken line part). On the other hand, as shown in FIG. 10(*c*), it is possible to judge that the surface roughness is not uniform and the state of polishing is not that good from profile information partially including a density level over a judgment line Th1.

In a semiconductor wafer 100 formed with a film, excessive polishing sometimes results in the film being ground off. In this case, a greater amount of light is reflected at the parts from which the film has been peeled off and the density level becomes lower. From this, for example, it is possible to set the offset value Δo found as explained above as the lower limit judgment level Tho. In this case, as shown by the broken line of FIG. 10(*b*) and, further, as shown in FIG. 10(*c*), from profile information including parts of a density level falling under the lower limit judgment line Tho, it is possible to judge that polishing has been performed over the endpoint of polishing. Furthermore, specifically, from the broken line parts of the profile information of FIG. 10(*b*), it is possible to judge that the surface roughness is relatively even, but that excessive polishing has been performed. From the profile information of FIG. 10(*c*), it is possible to judge that excessive polishing has partially been performed due to some sort of abnormality in the apparatus.

By the way, this surface roughness inspection system detects the surface roughness of the object based on the optically detected density information (area density value). Therefore, the effects of slant or offset of the semiconductor wafer 100 being inspected on the wafer rotary aligner 10 and, further, warping of the surface of the semiconductor wafer 10 etc. having nothing to do with surface roughness may also appear in the density information, so sometimes it is not possible to accurately judge the surface roughness from just the profile information of a single frequency characteristic. Due to the slant or offset etc. of the semiconductor wafer 100, the fluctuations appearing in the density information become relatively long in period. For that reason, the effects of slant or offset etc. of the semiconductor wafer appear in the profile information with a relatively long period. Further, the fluctuations appearing in the density information due to warping of the surface of the semiconductor wafer 100 become shorter in period compared with the case of a slant etc., but become longer in period compared with the case of the above-mentioned surface roughness. For that reason, the effects of warping of the surface of the semiconductor wafer 100 appear by a period of a medium length in the profile information.

If enlarging the window width W by 1 pixel at a time and generating profile information from the pixel density data acquired from the entire circumference of the end face of the semiconductor wafer 100, theoretically, as shown by FIG. 11(a) showing the case of a bare wafer and by (b) showing the case of a product wafer, it is possible to obtain profile information giving the shortest wavelength (high frequency) characteristic corresponding to one pixel pitch from profile information giving the longest wavelength (low frequency) characteristic where the scan position 0 degree to 360 degree becomes one wavelength, as shown by FIG. 12(a) showing the case of a bare wafer and by (b) showing the case of a product wafer.

In this way, from the profile information of the various frequency characteristics, one or more profile information are selected from the remaining profile information after eliminating the profile information of the relatively low frequency (large period) where the effects of the slant or offset etc. of the semiconductor wafer appear and profile information of the medium frequency (medium period) where the effects of warping of the surface of the semiconductor wafer 100 appear. Furthermore, the surface roughness and the state of polishing are judged overall by applying the above judgment levels (see FIG. 9 and FIG. 10) to that selected profile information.

Figure 13:
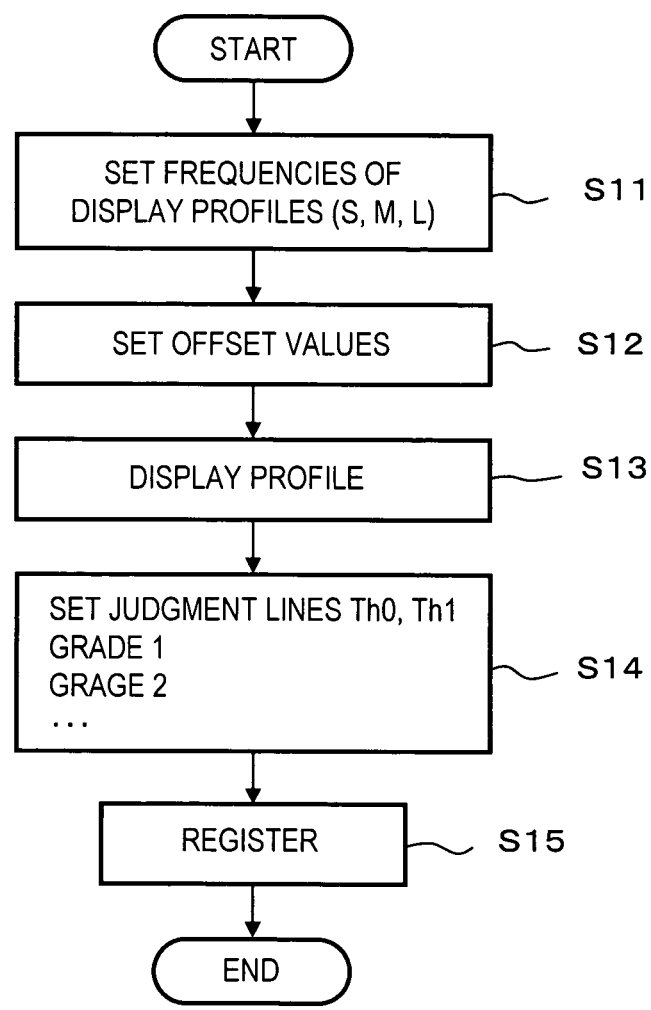
FIG. 13 is a flowchart showing processing for determining a judgment level used when judging the surface roughness from profile information.

By the way, as explained above, the judgment line used for judging the surface roughness can, for example, be determined in accordance with the routine shown in FIG. 13. In this case, the processing is performed on a semiconductor wafer 100 found to be good in advance (reference wafer).

Figure 11:
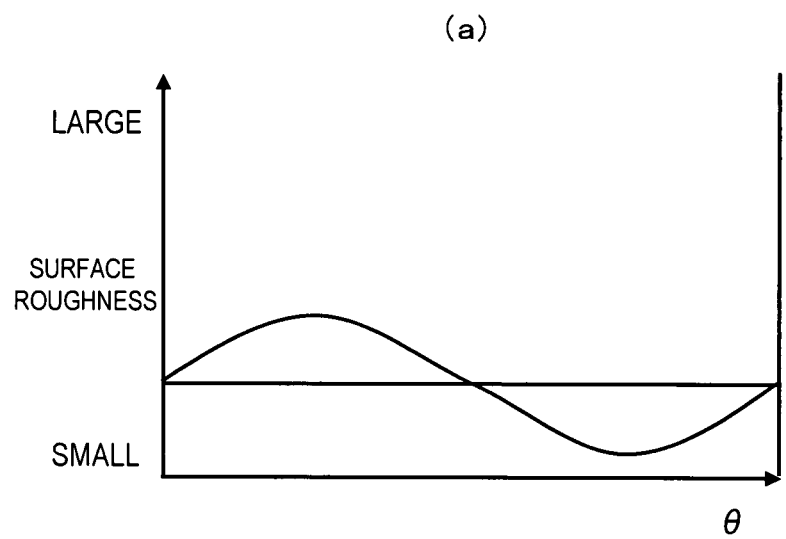
FIG. 11 is a view showing a model of profile information at the lowest frequency.
Figure 11:
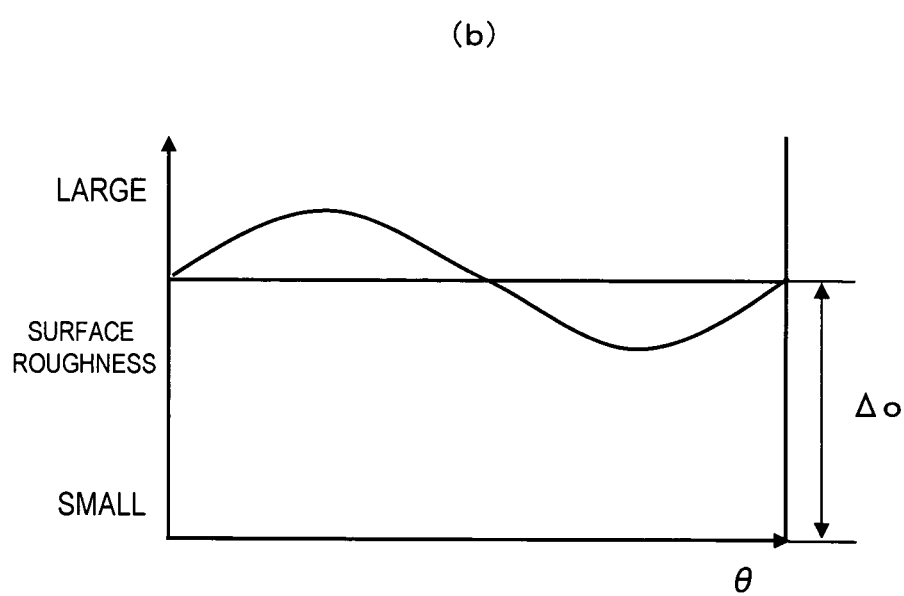
Figure 12:
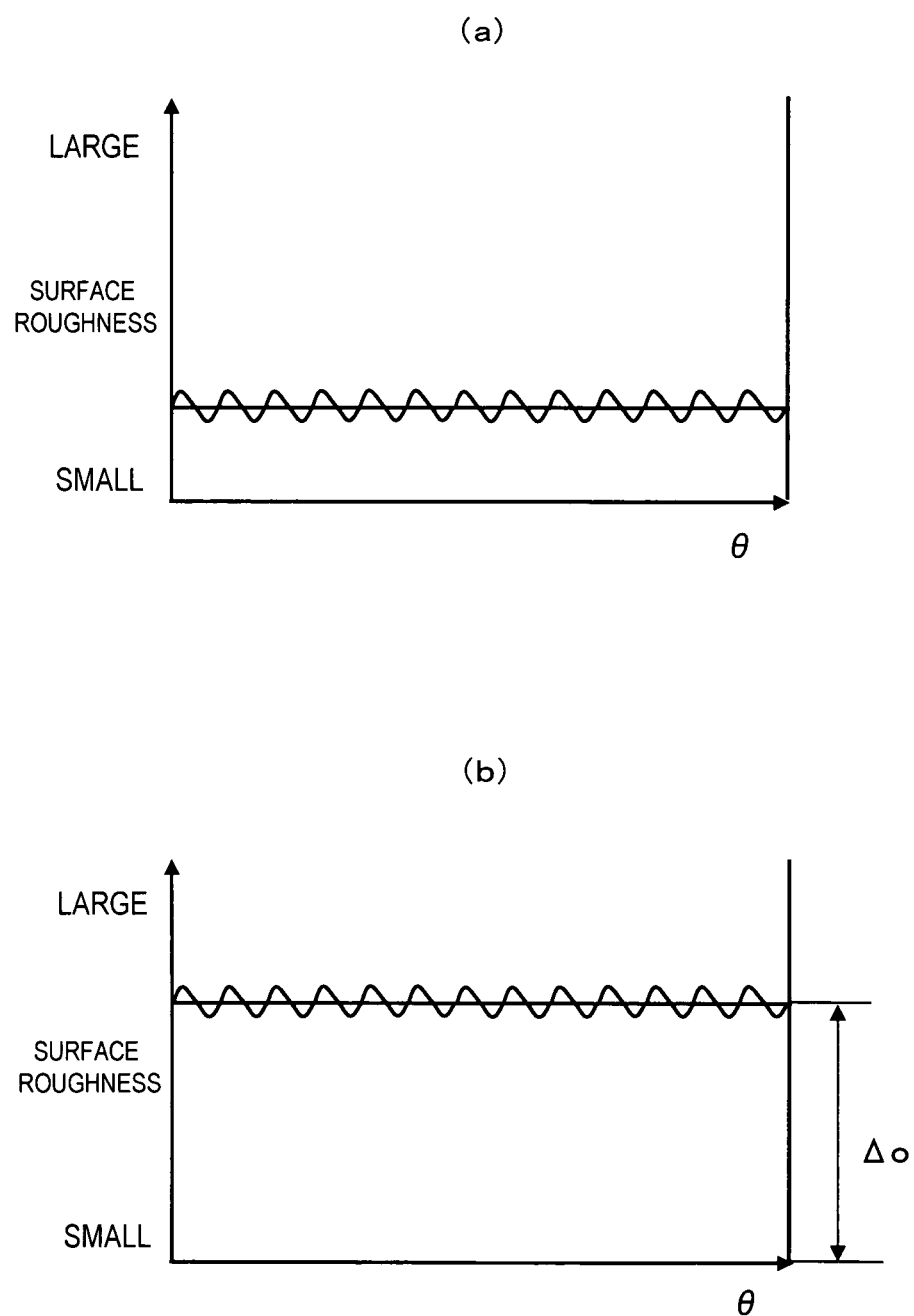
FIG. 12 is a view showing a model of profile information at a high frequency.

In FIG. 11, the frequency of the profile information to be displayed is set (S11). By changing the window width W for obtaining the area density value as explained above, it is possible to change the frequency characteristic of the profile information. If obtaining the area density value by a narrow window width, high frequency profile information (for example, see FIG. 12) can be obtained, while if obtaining the area density value by a wide window width, low frequency profile information (for example, see FIG. 11) can be obtained. Therefore, as the frequency of the profile information to be displayed, a relatively high frequency (S), medium frequency (M), and relatively low frequency (L) are set.

After this, as explained above, the density level which becomes substantially the same in a plurality of profile information and becomes the lowest level is set as the offset value Δo (S12). Furthermore, profile information of the three frequency characteristics set as explained above (for example, see FIG. 7) is displayed on the monitor unit 52 (S13). The operator can generally learn the state of setting of a semiconductor wafer 100 (slant, offset, etc.) from the lowest frequency (L) among the three profile information displayed on the monitor unit 52, can generally learn the state of warping of the peripheral end face of the semiconductor wafer 100 from the profile information of the medium frequency (M), and, furthermore, can generally learn the state of the surface roughness of the peripheral end of a semiconductor wafer 100 from the profile information of the highest frequency (S).

After this, the lower limit judgment level Tho is set based on the offset value Δo (S14). Further, the judgment level Th1 is determined in accordance with equation (1) using the level of fluctuation of the relatively high frequency profile information and the offset value Δo. A plurality of sets of judgment levels Th0, Th1 are determined in accordance with the grade of the surface roughness to be judged. The thus determined lower limit judgment levels Th0, Th1 are registered together with the ID identifying the reference wafer, the operator ID, and the time stamp (S15). For example, the above-mentioned judgment processing is performed using the registered judgment levels Tho, Th1 for the semiconductor wafers at the film-forming step, polishing step, etc.

INDUSTRIAL APPLICABILITY

As explained above, the surface roughness inspection system according to the present invention has the effect that the surface of an object being inspected can be suitably inspected even if a curved surface and is useful as a surface roughness inspection system detecting the roughness of the surface of an object being inspected such as the peripheral end face of a semiconductor wafer etc.

The invention claimed is:
1. A surface roughness inspection system comprising
an imaging unit comprising a line sensor, oriented to scan a surface of a disk being inspected in a direction perpendicular to a direction of extension of said line sensor, and outputting a density signal for each pixel from said line sensor,
a light source emitting light which is set so as to irradiate the surface of the disk, and
a processor processing a density signal from said line sensor of said imaging unit,
said processor comprising memory and a program for acquiring a pixel density value based on the density signal from said line sensor,
said processor including a density state generator generating density state information showing the state of density in a scan direction of the surface of the disk as information representing the roughness of the surface of the disk in the scan direction based on all of the pixel density values acquired for the surface of the disk, and
an output controller driving an output device to output the density state information generated by said density state generator,
wherein said line sensor is disposed to extend in a direction substantially perpendicular to the surface of the disk and the disk is turned about an axis vertical to the surface of the disk so as to scan a peripheral end face of said disk
wherein said density state generator
sets a window with respect to image information expressed by all of the pixel density values acquired for the surface of the disk in the scan direction, each window corresponding to one or more of plural scan positions along the peripheral end face of said disk,
calculates an area density value of each said window based on all of the pixel density values therein corresponding to a respective one or more of the scan positions, and generates said density state information based on the area density values corresponding to the respective scan positions, and wherein said output device controlled by said output controller outputs the density state information so as to indicate the area density values corresponding to the respective scan positions.

2. A surface roughness inspection system as set forth in claim 1, characterized in that said output controller includes a display controller driving a display unit to display a profile of density in a scan direction of the surface of the disk as said density state information.

3. A surface roughness inspection system as set forth in claim 1, characterized in that said processor includes a program for judging the roughness of the surface of the disk based on said density state information.

4. A surface roughness inspection system as set forth in claim 1, wherein the window is a one or more scan line window, and characterized in that and said processor shifts the one or more scan line window set with respect to the image information so as to correspond to each of the scan positions.

5. A surface roughness inspection system as set forth in claim 4, characterized in that said processor computes the sum of all pixel density values in said window as an area density value.

6. A surface roughness inspection system as set forth in claim 4, characterized by comprising a window setter setting a width of said window in said scan direction.

* * * * *